United States Patent [19]

Main

[11] Patent Number: 4,704,399

[45] Date of Patent: Nov. 3, 1987

[54] 1,3-DIOXAN-4-YLALKENOIC ACIDS

[75] Inventor: Brian G. Main, Sandbach, United Kingdom

[73] Assignee: Imperial Chemical Industries PLC, London, England

[21] Appl. No.: 670,018

[22] Filed: Nov. 9, 1984

[30] Foreign Application Priority Data

Nov. 11, 1983 [GB] United Kingdom ............... 8330097

[51] Int. Cl.$^4$ ................ A61K 31/335; C07D 319/06
[52] U.S. Cl. ................... 514/452; 549/375; 549/334; 549/333
[58] Field of Search ............ 549/375, 333, 334; 514/452

[56] References Cited

U.S. PATENT DOCUMENTS 2,992,234  7/1961  Acker ................................ 549/375
4,567,197  1/1986  Brewster et al. ................... 514/452

FOREIGN PATENT DOCUMENTS 0094239  11/1983  European Pat. Off. ............ 549/375
550391   8/1977   U.S.S.R. ............................. 549/375

*Primary Examiner*—Nicky Chan
*Attorney, Agent, or Firm*—Cushman, Darby & Cushman

[57] ABSTRACT

This invention concerns novel 1,3-dioxan-4-yl-alkenoic and alkanoic acids of formula I wherein Ra is (1–6C)alkyl, halogeno-(1–6C)alkyl, Rb is hydrogen or as Ra, or Ra and Rb together form (2–5C)polymethylene or (2–4C)oxypolymethylene, n is 2, 3 or 4, A is vinylene or ethylene, benzene ring B optionally bears a single substituent and the substituents at positions 4 and 5 of the dioxane ring have trans-relative stereochemistry; together with pharmaceutically acceptable salts, (1–6C)-alkyl esters and (1–6C)alkanesulphonamides thereof. The compounds of formula I are antagonists of thromboxane $A_2$ and are of value in treating a variety of disease conditions. The invention also provides processes for the manufacture of, and pharmaceutical compostions of, the compounds of formula I.

10 Claims, No Drawings

1,3-DIOXAN-4-YLALKENOIC ACIDS

The present invention concerns novel 1,3-dioxan-4-ylalkenoic and alkanoic acids which antagonise one or more of the actions of thromboxane $A_2$ (hereinafter "TXA2"), and are valuable therapeutic agents.

Certain 4-(hydroxyalkyl)-1,3-dioxan-trans-5-ylalkenoic acids are known (UK patent application No. 8004647, published as Ser. No. 2046733A) as inhibitors of the enzyme responsible for the synthesis of $TXA_2$ In addition, certain 6-(t-butoxyalkynyl)-2,2-dimethyl-1,3-dioxan-cis-4-ylalkenoic acids have been described by Fried and co-workers (*Advances in Prostaglandin* and *Thromboxane Research*, 1980, 6, 427–43) as inhibitors of various enzymes in the series of biochemical conversions known as the arachidonic acid cascade. We have now discovered that a series of (5-phenyl-1,3-dioxan-4-yl)alkenoic and alkanoic acids possesses thromboxane antagonist properties and this is the basis for our invention.

According to the invention there is provided a (5-phenyl-1,3-dioxan-4-yl)alkenoic or alkanoic acid derivative (hereinafter referred to as "an acid") of the formula I (set out hereinafter) wherein Ra is (1–6C)alkyl or halogeno(1–6C)alkyl; Rb is hydrogen, (1–6C)alkyl or halogeno(1–6C)alkyl;or Ra and Rb together form a (2–5C)polymethylene or (2–4C)oxypolymethylene group; n is 2, 3 or 4; A is vinylene or ethylene; benzene ring B optionally bears a 2-substituent selected from halogeno, methyl, hydroxy, trifluoromethyl and nitro, or bears a 4-methyl substituent; and the substituents at the 4 and 5 positions of the dioxane ring have trans-relative stereochemistry; or a pharmaceutically acceptable salt, (1–6C)alkyl ester or (1–6C)alkanesulphonamide of said acid of formula I.

It will be appreciated that the acids of formula I contain at least two asymmetric carbon atoms (i.e. the starred carbon atoms of the ring) and may exist and be isolated in racemic and optically active forms. In addition those acids of formula I wherein A is vinylene exist, and may be isolated, in separate stereoisomeric forms ('E' (trans) and 'Z' (cis)] about that group. It is to be understood that the present invention encompasses any racemic, optically active or stereoisomeric form (or mixtures thereof) which is capable of antagonising one or more of the actions of $TXA_2$, it being well known in the art how to prepare individual optical isomers (for example by synthesis from optically active starting materials or resolution of a racemic form) and individual 'E' and 'Z' stereoisomers (for example by chromatographic separation of a mixture thereof), and how to determine the $TXA_2$ antagonist properties using the standard test described hereafter.

In this specification, the terms Ra and Rb etc, are used to depict generic radicals and have no other significance.

A particular value for Ra or Rb when it is (1–6C)alkyl is, for example, methyl, ethyl, propyl, isopropyl or t-butyl and when it is halogeno(1–6C)alkyl is, for example, chloromethyl, 2-chloroethyl, trifluoromethyl or 2,2,2-trifluoroethyl.

A particular value for Ra and Rb when together they form a (2–5C)polymethylene or (2–4C)oxypolymethylene group is, for example trimethylene, tetramethylene, pentamethylene, trimethyleneoxy, methyleneoxyethylene or ethyleneoxyethylene.

A particular value for a 2-halogeno substituent which may be present on benzene ring B is for example, a 2-fluoro, 2-chloro or 2-bromo substituent.

A preferred value for n is 3 and for A is ethylene.

One preferred group of compounds according to the invention comprises those acids of the formula I wherein n is 3, A is ethylene or cis-vinylene and Ra, Rb and benzene ring B have any of the meanings defined above; and the substituents at positions 4 and 5 of the dioxane ring have trans-relative stereochemistry; together with the pharmaceutically acceptable salts thereof; and the (1–6C)alkyl esters and (1–6C)alkanesulphonamides of said acids of formula I.

A further preferred group of compounds according to the invention comprises those acids of the formula I wherein n is 3, A is ethylene or cis-vinylene, Ra is (1–4C)alkyl or trifluoromethyl, Rb is hydrogen, benzene ring B is selected from phenyl, o-tolyl and o-fluoro-, o-chloro-, o-hydroxy- and o-trifluoromethyl-phenyl and the substituents at positions 4 and 5 of the dioxane ring have trans-relative stereochemistry; together with the pharmaceutically acceptable salts thereof; and the (1–6C)alkyl esters and (1–6C)alkanesulphonamides of said acids of formula I.

Specific values for benzene ring B include, for example, phenyl, 2-methylphenyl, 2-fluorophenyl, 2-chlorophenyl, 2-bromophenyl, 2-hydroxyphenyl, 2-trifluoromethylphenyl, 2-nitrophenyl and 4-methylphenyl.

Particular pharmaceutically acceptable salts of acids of formula I are, for example, alkali metal and alkaline earth metal salts such as lithium, sodium, potassium, magnesium and calcium salts, aluminium and ammonium salts, and salts with organic amines and quaternary bases forming physiologically acceptable cations, such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

Particular (1–6C)alkyl esters of acids of formula I are, for example, methyl, ethyl, propyl or butyl esters.

A preferred ester is, for example, a methyl ester.

Particular (1–6C)alkanesulphonamides of acids of formula I are, for example, methanesulphonamides and ethanesulphonamides.

Typical compounds of the invention are described in the accompanying Examples. Of these, those compounds described in Example 3, 12, 14 and 22 are presently preferred.

The compounds of the invention may be manufactured by conventional procedures of organic chemistry well known in the art for the production of structurally analogous compounds. Such processes are provided as a further feature of the invention and are illustrated by the following preferred procedures in which Ra, Rb, A, benzene ring B and n, have any of the aforesaid meanings:

(a) For an acid of formula I wherein A is vinylene, an aldehyde of the formula II is reacted with a Wittig reagent of the formula:

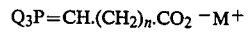

$Q_3P=CH.(CH_2)_n.CO_2{}^-M^+$ wherein Q is (1–6C)alkyl or aryl (especially phenyl) and $M^+$ is a cation, for example an alkali metal cation such as the lithium, sodium or potassium cation.

The process in general produces compounds of formula I in which the substituents adjacent to the double bond have predominantly cis-relative stereochemistry i.e. the "Z" isomer. However, the compounds of formula I having trans-relative stereochemistry may also be obtained from the process by conventional separation of the mixture of cis- and trans- isomers first obtained.

The process is conveniently performed in a suitable solvent or diluent, for example an aromatic solvent such as benzene, toluene or chlorobenzene, an ether such as 1,2-dimethoxyethane, dibutyl ether or tetrahydrofuran, in dimethyl sulphoxide or tetramethylene sulphone, or in a mixture of one or more such solvents or diluents. The process is generally performed at a temperature in the range, for example, $-80°$ C. to $40°$ C. but is conveniently performed at or near room temperature, that is in the range 15 to $35°$ C.

(b) For a compound of formula I wherein A is ethylene, an acid of formula I wherein A is vinylene, or a salt, ester or sulphonamide thereof as defined above, is hydrogenated in the presence of a suitable catalyst.

The process may be carried out in a suitable solvent or diluent, for example a (1–4C)alkanol such as ethanol or 2-propanol, optionally in the presence of water, and at a temperature in the range, for example, 15 to $35°$ C. using hydrogen at a pressure of, for example, 1 to 2 atmospheres.

A suitable catalyst is, for example, a noble metal catalyst such as palladium metal, conveniently on an inert support such as carbon, barium sulphate or barium carbonate.

(c) A threo-diol derivative of the formula III wherein one of Qa and Qb is hydrogen and the other is hydrogen, alkanesulphonyl or arenesulphonyl, or a group of the formula $—CRR^1$ OH (wherein R and $R^1$ are the same or different alkyl) or an ester or sulphonamide thereof (as defined hereinbefore for acids of formula I), is reacted with a carbonyl compound of the formula RaRb.CO, or an acetal, hemiacetal or hydrate thereof.

The carbonyl compound of the formula RaRb.CO [or its hydrate, or its acetal or hemiacetal with a (1–4C)alkanol such as methanol or ethanol]is preferably used in excess.

A suitable value for Qa or Qb when it is alkanesulphonyl is, for example, methanesulphonyl or ethanesulphonyl and when it is arenesulphonyl is, for example, benzenesulphonyl or p-toluenesulphonyl. A suitable value for R or $R^1$ is, for example, methyl or ethyl.

Depending on the nature of Qa and Qb different reaction conditions are necessary. Thus, when Qa and Qb are both hydrogen or when one is a group of the formula $—CRR^1$ OH and the other is hydrogen, the reaction is carried out in the presence of an acid catalyst, for example, hydrogen chloride, hydrogen bromide, sulphuric acid, phosphoric acid, p-toluenesulphonic acid or the anionic form of a sulphonated polystyrene catalyst, conveniently in a suitable solvent or diluent, for example an ether such as diethyl ether, dibutyl ether, 1,2-dimethoxyethane or tetrahydrofuran, and at a temperature in the range, for example, 10 to $120°$ C.

Similarly, when one of Qa and Qb is alkanesulphonyl or arenesulphonyl and the other is hydrogen, the reaction is carried out first in the presence of an acid catalyst, for example under the conditions described above to produce an intermediate of the formula III, wherein one of Qa and Qb is alkanesulphonyl or arenesulphonyl, and the other is a group of the formula —CRaRb.OH. The latter intermediate may then be cyclised in situ to the required compound of formula I by addition of a base, for example, sodium hydride, butyllithium or potassium carbonate, in a suitable solvent or diluent, for example in the ether solvent used for the acid catalysed step above, and at a temperature in the range, for example, 30–100° C. It will be appreciated that the above mentioned intermediate may also be isolated, characterised and separately cyclised under the influence of strong base to give a compound of formula I. Such a procedure is encompassed by the invention.

Those starting materials of formula III wherein Qa and Qb are both hydrogen may be obtained by mild hydrolysis or alcoholysis of the dioxane ring of an acid compound of formula I, for example, in which Ra and Rb are both methyl or ethyl radicals, obtained by another process described herein. This reaction will normally be carried out at a temperature in the range, for example, 15–100° C. and conveniently, at or near room temperature, using an aqueous mineral acid such as hydrochloric acid in a suitable solvent such as tetrahydrofuran, ethanol or 2-propanol. Alternatively, the starting materials of formula III wherein Qa and Qb are both hydrogen may be made by a synthesis starting with the appropriate substituted phenylacetic acid as illustrated in Example 4 hereinafter.

The starting materials of formula III wherein one of Qa and Qb is a group of the formula $—CRR^1.OH$ and the other is hydrogen, are generally obtained as intermediates in the above mentioned formation of the threo-diol of formula III (Qa=Qb=H) and are not normally isolated or characterised.

The starting materials of formula III wherein one of Qa and Qb is alkanesulphonyl or arenesulphonyl and the other is hydrogen, may be obtained from the corresponding threo-diol of formula III (Qa=Qb=H) by reaction with one molecular equivalent of the appropriate alkanesulphonyl or arenesulphonyl halide, for example methanesulphonyl chloride or p-toluenesulphonyl chloride, in a suitable solvent or diluent (such as an ether or dichloromethane) and in the presence of a base such as pyridine or triethylamine.

When the starting material of formula III is a carboxylic acid, some degree of reaction at the acid moiety may occur during process (c) necessitating hydrolysis [according to process (e) hereinafter] as a final step before isolation of the required end-product.

(d) An acid of formula I, or an ester or sulphonamide as defined hereinbefore, in which Ra and Rb are methyl or ethyl is reacted with an excess of a compound of the formula RaRb.CO or an acetal, hemiacetal or hydrate thereof, in the presence of an acid-catalyst.

It will be appreciated that this procedure is related to process (c) above. As a result, generally the same reaction conditions may be employed. Thus, for example, a suitable acid-catalyst is p-toluenesulphonic acid, and a suitable solvent such as tetrahydrofuran may conveniently be employed with a reaction temperature in the range 10° to 120° C. When a (1–6C)alkyl ester is used, it is preferable to employ an acetal or hemiacetal derivative formed from the corresponding (1–6C)alkanol.

(e) A compound of the formula IV wherein Z is alkoxycarbonyl (especially methoxycarbonyl or ethoxycarbonyl), phenoxycarbonyl, benzyloxycarbonyl, cyano or carbamoyl is hydrolysed.

The hydrolysis is conveniently carried out under the influence of base, for example an alkali metal hydroxide (such as lithium, potassium or sodium hydroxide) in a suitable aqueous solvent, for example a (1–4C)alkanol (such as methanol or ethanol) or a glycol (such as ethylene glycol) at a temperature in the range, for example, 15° to 150° C. In general higher reaction temperatures are required when Z is cyano or carbamoyl.

(f) For an acid of formula I wherein benzene ring B is 2-hydroxyphenyl, a corresponding derivative of said compound wherein the hydroxy substituent is protected by a trimethylsilyl, (1-6C)alkyl (such as methyl or ethyl), acyl (such as acetyl or benzoyl) or benzyl protecting group, is deprotected.

The deprotection conditions required necessarily depend on the protecting groups concerned. Thus, for example, when it is methyl or ethyl the deprotection may be carried out, for example, by heating with sodium thioethoxide in a suitable solvent (such as N,N'-dimethylpropyleneurea or N,N-dimethylformamide) at an elevated temperature, for example 60°–160° C. Similarly, when the protecting group is acyl, it may be removed, for example, by hydrolysis in the presence of a base (such as sodium or potassium hydroxide) in a suitable aqueous solvent [such as a (1–4C)alkanol or a glycol] at a temperature in the range, for example, 10°–60° C. Similarly, in the case of a trimethylsilyl protecting group, it may be removed for example, by reaction with aqueous tetrabutylammonium fluoride or sodium fluoride in conventional manner. When the protecting group is benzyl it may be removed, for example, by reaction with sodium in liquid ammonia or by hydrogenation in the presence of a platinum or palladium catalyst. The latter procedure is particularly convenient when a compound of formula I wherein A is ethylene is required since a starting material in which A is vinylene or ethylene may then be used.

The necessary protected derivatives of the formula I compounds may be made by analogy with the other processes described herein. Similarly, the necessary starting materials for processes (a)–(e) may be obtained by conventional procedures well known in the art of organic chemistry. These procedures are illustrated in the accompanying reaction Schemes and Examples. In general, a mixture of stereoisomers is produced in the reaction Schemes and it is necessary to separate out the individual stereoisomers using a conventional procedure, such as chromatography, at one or more stages in the Schemes.

The necessary Wittig reagents may be obtained by conventional procedures, for example by treating the corresponding phosphonium halides with a strong base such as sodium hydride, lithium diisopropylamide, potassium t-butoxide or butyllithium. They are generally formed in situ just prior to carrying out the condensation process (a).

Whereafter, when an ester or sulphonamide is required, the corresponding acid of formula I, conveniently as a reactive derivative thereof (such as its acid chloride, bromide, anhydride, mixed anhydride with formic acid or azide), is reacted with the appropriate (1-6C)alkanol or (1-6C)alkanesulphonamide, with an alkali metal salt thereof.

Such a procedure may be carried out under conventional conditions, for example using an excess of the alkanol or sulphonamide in a suitable solvent, for example tetrahydrofuran or 1,2-dimethoxyethane, and at a temperature in the range, for example, 10° to 100° C. When a free acid of formula I is used, a suitable dehydrating agent such as dicyclohexylcarbodiimide is normally added to facilitate the reaction. A suitable solvent or diluent which may then be used is, for example, tetrahydrofuran, pyridine, acetone, dichloromethane or 1,2-dimethoxyethane. When an alkali metal salt of a (1-6C)alkanol or (1-6C)alkanesulphonamide is employed, it is generally preferred to carry out the reaction in the presence of a polar solvent such as N,N-dimethylformamide or hexamethylphosphoramide. It is not normally necessary to provide external heating for those procedures in which a reactive derivative of an acid of formula I is employed.

When a salt of an acid of formula I is required, it s obtained by reaction with the appropriate base affording a physiologically acceptble cation, or by any other conventional procedure.

Further, when an optically active form of an acid of formula I is required, one of the aforesaid processes is carried out using an optically active starting material. Alternatively, the racemic form of the said acid may be reacted with an optically active form of a suitable organic base, for example ephedrine, N,N,N-trimethyl (1-phenylethyl)ammonium hydroxide or 1-phenylethylamine, followed by conventional separation of the diastereoisomeric mixture of salts thus obtained, for example by fractional crystallisation from a suitable solvent, for example a (1-4C)alkanol, whereafter the optically active form of said acid of formula I may be liberated by treatment with acid using a conventional procedure, for example using an aqueous mineral acid such as dilute hydrochloric acid.

When an optically active form of a derivative of an acid of formula I is required, it may be obtained, for example, using the aforementioned esterification or amidification procedures starting from the appropriate optically active form of said acid.

Many of the intermediates defined herein are novel and are provided as further separate features of the invention.

As stated earlier, the acids of formula I are antagonists of one or more of the actions of $TXA_2$, for example certain of its actions on blood platelets, the vasculature and/or the lung. The antagonism may be demonstrated in one or other of the following standard tests:

(a) The rabbit aortal strip model devised by Piper and Vane (*Nature*, 1969, 223, 29-35) using as agonist the $TXA_2$ mimetic agent known as U46619 (R. L. Jones et alia in "Chemistry, Biochemistry and Pharmacological Activity of Prostanoids", eds. S. M. Roberts and F. Scheinmann, at p.211; Pergamon Press, 1979);

(b) a blood platelet aggregation test based on that described by Born (*Nature*, 1962, 194, 927-929) and involving measuring the inhibition by a test compound of aggregation of citrated, platelet rich human plasma induced by a sub-maximal concentration (in the range 25-100 μg./ml.) of arachidonic acid; and (c) a bronchoconstriction test involving measuring the inhibition by a test compound of the bronchoconstriction induced in the Konzett-Rossler guinea-pig model (as modified by Collier and James, *Brit. J. Pharmacol.*, 1967, 30, 283-307) by intravenous administration of the $TXA_2$ mimetic agent, U46619 at 1-1.5 μg/kg.

Similarly, the antagonism of the effects of $TXA_2$ on the vasculature may be demonstrated in the following manner:

(d) Male rats (Alderley Park strain) are anaesthetised with sodium pentobarbital and blood pressure is monitored at the carotid artery. The $TXA_2$ mimetic agent U46619 is administered intravenously via the jugular vein and an $ED_{50}$ (dose necessary to produce 50% of the maximum hypertensive effect) is established (n=3). The $ED_{50}$ for U46619 is approximately 5 μg/kg. A test compound is then administered either intravenously via the jugular vein or orally via a cannula directly into the stomach and the animal challenged with an $ED_{50}$ dose of U46619, five minutes after dosing with test compound and then successively every ten minutes until the hypertensive effect of U46619 is no longer blocked.

In general, compounds of formula I show significant activity in one or more of the above tests without any sign of overt toxicity at the active dose in tests (c) or (d). By way of example, the compound of formula I described in Example 12 hereinafter gives a $pA_2$ of 6.7 in test (a), significant reduction of bronchoconstriction in test (c) some 3 hours following an oral dose of 5mg/kg., and complete inhibition of the hypertensive effect in test (d) 80-90 minutes following an oral dose of 50 mg./kg.

As stated previously, the compounds of formula I may be used in the therapy or prevention of diseases or adverse conditions in warm-blooded animals in which it is desirable to antagonise one or more of the actions of $TXA_2$. In general, a compound of formula I will be administered for this purpose by an oral, rectal, intravenous, subcutaneous, intramuscular or inhalation route, so that a dose in the range, for example 0.05-20 mg/kg. body weight, will be given up to four times per day, varying with the route of administration, the severity of the condition and the size and age of the patient under treatment.

The compounds of formula I will generally be used in the form of a pharmaceutical composition comprising a compound of formula I or, where appropriate, a salt thereof as defined hereinbefore, together with a pharmaceutically acceptable diluent or carrier. Such compositions are provided as a further feature of the invention and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection; in the form of aerosols or nebuliser solutions or suspensions for administration by inhalation; and in the form of powders together with pharmaceutically acceptable inert solid diluents such as lactose for administration by insufflation.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The pharmaceutical compositions of the invention may also contain one or more agents known to be of value in diseases or conditions intended to be treated; for example, a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an antihistamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

In addition to their use in therapeutic medicine the compounds of formula I are also useful as pharmacological tools in the development and standardisation of test systems for the evaluation of the effects of $TXA_2$ in laboratory animals such as cats, dogs, rabbits, monkeys, rats and mice, as part of the search for new therapeutic agents. The compounds of formula I may also be used because of their $TXA_2$ antagonist properties in helping to maintain the viability of blood and blood vessels in warm-blooded animals (or parts thereof) under-going artificial extracorporeal circulation, for example during limb or organ transplants. When used for this purpose a compound of formula I or a physiologically acceptable salt thereof will generally be administered so that a steady state concentration in the range, for example, 0.5 to 50 mg. per litre is achieved in the blood.

The invention will now be illustrated by the following non-limiting Examples in which, unless otherwise stated:

(i) evaporations were carried out by rotary evaporation in vacuo;

(ii) operations were carried out at room temperature, that is in the range 18°-26° C.;

(iii) column chromatography was performed on Merck Kieselgel 60 (Art, 7734) using approximately 50-70 g. of $SiO_2$ per g. of sample, and monitoring the process by thin layer chromatography on Merck 0.25 mm. Kieselgel 60F 254 plates (Art. 5715), flash chromatography was performed on Merck Kieselgel (Art 9385); these materials were obtained from E. Merck, Darmstadt, W. Germany;

(iv) yields are given for illustration only and are not necessarily the maximum attainable;

(v) NMR spectra were normally determined at 90 MHz in $CDCl_3$ using tetramethylsilane (TMS) as an internal standard, and expressed as chemical shifts (delta values) in parts per million relative to TMS using the following abbreviations for designation of major peaks: s, singlet; m, multiplet; t, triplet; d, doublet; br, broad; when a single value is given for a multiplet (m) this corresponds to the centre of the signals making up the multiplet; and (vi) end-products were isolated as racemates, and characterised by NMR and mass spectroscopy and other standard procedures.

EXAMPLE 1

A mixture of (4-carboxybutyl)triphenyl phosphonium bromide (57.4 g.) and potassium t-butoxide (29.1 g.) in anhydrous tetrahydrofuran (THF) (250 ml.) was stirred under argon for 30 minutes and then (2,2-dimethyl-5-o-tolyl-1,3-dioxan-trans-4-yl)acetaldehyde (8.5 g.) added with cooling to 10° C. After 1 hour of stirring the mixture was added to water (1 l.) and the aqueous mixture washed with ether. The aqueous phase was separated, acidified to pH 4 (HCl) and extracted with ether (4×150 ml.). The combined extracts were washed with water (150 ml.), dried ($MgSO_4$) and evaporated. The yellow oil was purified twice by column chromatography, first using ether as eluant and then using 1:3 v/v ether/hexane as eluant. There was thus obtained 5(Z) 7-(2,2,-dimethyl-5-o-tolyl-1,3-dioxan-trans-4-yl)heptenoic acid as a colourless oil (4.7 g.) NMR: 1.5 (6H,2s), 1.6-2.3(8H,m), 2.4 (3H,s), 3.1 (1H,m), 3.3-4.3 (3H,m), 5.4 (2H,m), 7.1 (4H,s); m/e (chemical ionisation): 330 ($M^++H$), 350 ($M^++NH_4$) [Note: $C^{13}$NMR indicates this material to contain aproximately 15% of the 5(E) olefinic isomer.]

The necessary starting material may be obtained as follows:

(a) A solution of o-tolylacetic acid (45.0 g.) in dry THF (300 ml.) was treated under argon at 5°-10° C. with a 1.60M solution (376 ml.) of butyl lithium. The suspension was stirred 2 hours at 5°-10° C. and then acrolein (dried over 3A molecular sieve) (20.0 ml., 16.8 g.) was added over 5 minutes. The mixture was stirred for 2 hours and then carefully treated with ice-water (1 l.) The aqueous mixture was washed with ether (200 ml.). The aqueous layer was separated and acidified to pH4 (HCl) and extracted with ether (3×150 ml.). The extracts were washed with water, dried (magnesium sulphate) and evaporated to give 3-hydroxy-2-o-tolyl-4-pentenoic acid (A) (55.2 g.), which was used without purification.

(b) A solution of A (55.2 g.) in toluene (250 ml.) was treated under argon at 10°-20° C. with a 3.4M solution (120 ml.) of sodium bis(2-methoxyethoxy)aluminium hydride ("Red-Al") in toluene. After stirring for 16 hours the reaction mixture was carefully quenched with water. Solid was removed by filtration and the filter cake was washed well with ether. The aqueous filtrate was extracted with ether. The combined organic phases were washed well with saturated sodium bicarbonate solution then with water, dried ($MgSO_4$) and evaporated to give an oil. This was purified by column chromatography using ether/petrol (40°-60°) and then ether as eluant, to give threo-3-hydroxy-2-o-tolyl-4-penten-1-ol (B) as an oil (15.0g., 29%).

(c) A solution of B (15.0 g.) in 1,1-dimethoxypropane (100 ml.) was treated with p-toluenesulphonic acid (20 mg.). After 30 minutes the mixture was poured into saturated sodium bicarbonate solution (50 ml.) and the whole extracted with ether (3×100 ml.). The combined extracts were washed with saturated sodium bicarbonate solution (50 ml.), then with water (50 ml.), dried ($MgSO_4$) and evaporated to give [4,5-trans]-2,2,-dimethyl-5-o-tolyl-4-vinyl-1,3-dioxane (C) as a pale yellow oil (18.4 g.) which was used without purification.

(d) A solution of C. (18.4 g.) in dry THF (100 ml.) was treated at 0-5° C. under argon with a 0.5M solution (175 ml.) of 9-borabicyclo[3.3.1] nonane (9-BBN) in hexane. The mixture was left for 19 hours at room temperature, then ice-cooled and treated carefully with water (120 ml.), 2M sodium hydroxide solution (120 ml.) and then hydrogen peroxide (30% w/w, 50 ml.). After 30 minutes the mixture was diluted with water (500 ml.) and then extracted thoroughly with ether. The combined extracts were washed with water, dried ($MgSO_4$) and evaporated to give [4,5-trans]-4-(2-hydroxyethyl)-2,2-dimethyl-5-o-tolyl dioxane(D) as an oil (21.0 g.) which was used without purification.

(e) D(21.0 g.) was added to a stirred mixture of pyridine (7.6 ml., 7.46 g.) and trifluoroacetic acid (3.4 ml., 5.21 g.) in dimethylsulphoxide (DMSO) (125 ml.) at 5°-10° C. Dicyclohexylcarbodi-imide (DCCI; 19.0 g.) was then added. Stirring was continued at room temperature for 16 hours and then further DCCI (6.9 g.) was added. After a further 3.5 hours, oxalic acid was added in portions until effervescence stopped. The mixture was diluted with ether (200 ml.). Solid was removed by filtration and the filtrate washed successively with 1M hydrochloric acid (rapid treatment), saturated sodium bicarbonate solution and water, dried ($MgSO_4$) and evaporated. The residue was purified by column chromatography using methylene chloride as eluant to give (2,2-dimethyl-5-o-tolyl-1,3-dioxan-trans-4-yl)acetaldehyde (8.6 g.) which was pure by thin layer chromatographic and NMR spectrocopic analysis.

EXAMPLE 2

A solution of 5(Z)-7-(2,2,-dimethyl-5-o-tolyl-1,3-dioxan-trans-4-yl)heptenoic acid (3.32 g.) in ethanol (50 ml.) was hydrogenated in the presence of platinum (IV) oxide (Adam's catalyst; 100 mg.) at atmospheric pressure during 2 hours. The catalyst residue was removed by filtration and the filtrate was evaporated to give a colourless syrup which rapidly crystallised. This material was purified by column chromatography using 1:1 v/v ether/hexane as eluant to give 7-(2,2-dimethyl-5-o-tolyl-1,3-dioxan-trans-4-yl)heptanoic acid as a solid (1.16 g.), m.p. 89°-91° C. (after recrystallisation from hexane); NMR: 1.3 (10H,m), 1.5 (6H,2s), 2.3 (5H,m), 3.1 (1H,m), 3.8-4.2 (3H,m), 7.2 (4H,s).

EXAMPLE 3

A solution of 7-(2,2-dimethyl-5-o-tolyl-1,3-dioxan-trans-4-yl)heptanoic acid (336 mg.) in dry THF (2 ml.) and isobutyraldehyde (1 ml.) containing p-toluenesulphonic acid (10 mg.) was prepared. After 5 days ether (50 ml.) was added and the mixture washed with saturated sodium bicarbonate solution (30 ml.), dried ($MgSO_4$) and evaporated. The oil obtained was stirred for 18 hours with 2M sodium hydroxide (5 ml.) and methanol (5 ml.) and then diluted with water (100 ml.). The mixture obtained was washed with ether (25 ml.). The aqueous phase was acidified to pH 4 (HCl) and extracted thoroughly with ether. The combined extracts were washed with water, dried (MgS04) and evaporated to give 7-([2,4-cis,4,5 trans]-2-isopropyl-5-o-tolyl-1,3-dioxan-4 -yl)heptanoic acid as an oil which crystallised on standing to give a solid which was crystallised from hexane to give material (160 mg.) of m.p. 95-97° C., NMR: 1.0 (6H,d), 1.1-2.1 (11H,m), 2.4 (5H,m), 3.1 (1H,m), 3.6-4.2 (3H,m), 4.4 (1H,d), 7.2 (4H,s); m/e (chemical ionisation: 349 ($M^+ + H$), 366 ($M^+ + NH_4$)

EXAMPLE 4

A mixture was prepared of methyl threo-8-hydroxy-9-hydroxymethyl-9-o-tolylnonanoic acid (1.4 g.) in 2,2-dimethoxypropane (10 ml.) containing p-toluenesulphonic acid (10 mg.). After 5 minutes the mixture was diluted with ether (100 ml.) and saturated sodium bicarbonate solution (10 ml.). The ether phase was separated, washed with water, dried ($MgSO_4$) and evaporated. The oil obtained (containing the methyl ester of the end-product below) was stirred with 1M lithium hydroxide solution (10 ml.) and methanol (10 ml.) for 18 hours and then diluted with water (50 ml.). The aqueous mixture was washed with ether. The separated aqueous phase was acidified to pH 4 (AcOH) and extracted with ether. The combined extracts were washed with water, dried ($MgSO_4$) and evaporated to give 7-(2,2-dimethyl 5-o-tolyl-1,3-dioxan-trans-4-heptanoic acid as a solid (0.4 g.), m.p. 91°-92° C. (after recrystallisation from hexane); m/e (chemical ionisation): 335 ($M^+ + H$), 352 ($M^+ + NH4$); NMR identical to that obtained for the same compound obtained as described in Example 2.

The starting material may be obtained as follows:

(a) o-Tolylacetic acid (4.56 g.) in THF (50 ml.) was treated at 5°-10° C. under argon with a 1.6M solution (36.0 ml.) of butyllithium in hexane. After 1 hour the solution obtained was added dropwise to a solution of methyl 7-formylheptanoate (5.68 g.) in dry THF (50 ml.) at −30° to −50° C. during 30 minutes. The mixture was stirred for 1.5 hours at the same temperature. Acetic acid (3.5 ml.) was then added carefully and the mixture was evaporated. The residue was partitioned between ether (100 ml.) and saturated sodium bicarbonate solution (50 ml.). The aqueous layer was acidified to pH 4 (HCl) and extracted thoroughly with ether. The combined extracts were washed with water, dried (MgSO$_4$) and evaporated. The residual oil was purified by medium pressure liquid chromatography on silica (190 g.), eluting with 30% v/v ethyl acetate/hexane, to give methyl 9-carboxy-8-hydroxy-9-o-tolylnonanoate (A) as an oil (1.94 g., single diastereoisomer);NMR : 1–1.7 (10H,m), 2.1–2.5 (5H,m), 3.6 (3H,s), 3.8–4.3 (2H,m), 6.7 (2H,br s), 7.2 (4H,s); m/e (chemical ionisation): 323 (M$^+$+H), 340 (M$^+$+NH$_4$).

(b) A solution of A (1.9 g.) in dry THF (30 ml.) was treated under argon with a 1M solution (12.0 ml.) of borane in THF. After 2 hours a further portion (6.0 ml.) of borane in THF was added. After a further 30 minutes the reaction was quenched by careful addition of methanol (2 ml.) and acetic acid (2 ml.). The mixture was then evaporated to give an oil. This was dissolved in ether (100 ml.). The solution obtained was successively washed with 2M hydrochloric acid (20 ml.), saturated sodium bicarbonate solution, water, then dried (MgSO$_4$) and evaporated to give methyl threo-8-hydroxy-9-hydroxymethyl-9-o-tolylnonanoate as an oil (1.4 g.) which was suitable for use without purification.

EXAMPLES 5–6

Using a similar procedure to that described in Example 1 but starting from (2,2-dimethyl-5-phenyl-1,3-dioxan-trans-4-yl)acetaldehyde there was obtained 5(Z)-7-(2,2 dimethyl-5 phenyl-1,3-dioxan-trans-4-yl)heptenoic acid (Example 5) as a colourless oil; NMR: 1.5–2.3 (14H,m), 2.8 (1H,m) 3.9(3H,m), 7.2 (5H,m), 9.2 (1H,broad s) [containing approx 20% of the 5(E) isomeric acid by $^{13}$C. NMR]; m/e : 303 (M$^+$—CH$_3$)

The starting material was obtained by the same procedure as described in Example 1, starting from phenylacetic acid and going through the following intermediates:

(a) 3-hydroxy-2-phenyl-4-pentenoic acid, as an oil; NMR: 3.6(1H,t), 4.5–5.9 (4H,m), 7.25 (5H,s);

(b) threo-3-hydroxy-2-phenyl-4-penten-1-ol [used without characterisation];

(c) [4,5-trans]-2,2-dimethyl-5-phenyl-4-vinyl-1,3-dioxane, as an oil; NMR: 1.5 (6H,d), 2.8 (1H,2t), 3.7–4.2 (2H,m), 4.5 (1H,2d), 4.9–5.2(2H,m), 5.5–5.9 (1H, m), 7.2 (5H,s); m/e : 203 (M$^+$—CH$_3$);

(d) [4,5-trans]-4-(2-hydroxyethyl)-2,2-dimethyl-5-phenyl-1,3-dioxane, as an oil; NMR: 1.4–1.9 (8H,m), 2.8 (1H,2t), 3.5–4.5 (5H,m), 7.2 (5H,s); m/e: 221 (M$^+$—CH$_3$); and (e) (2,2-dimethyl-5-phenyl-1,3-dioxan-trans-4-yl)-acetaldehyde, as an oil; NMR: 1.5 (6H,d), 2.0 (1H,s), 1.35 (1H,m), 2.8 (1H,2t), 3.7–4.2 (2H,m), 4.4–4.7 (1H,m), 7.2 (5H,s), 9.6 (1H,s); m/e : 235 (M$^+$+H), 219 (M$^+$—CH$_3$)

Using an analogous procedure, 5(Z)-7-(2,2-dimethyl-5-p-tolyl-1,3-dioxan-trans-4-yl)-heptenoic heptenoic acid (Example 6) was obtained as an oil, which slowly solidified to give material of m.p. 56°–58° C.; NMR: 1.2–2.3 (17H,m), 2.8 (1H,m), 3.7–4.1 (3H,m), 5.2–5.7 (2H,m), 7.1 (4H,m); starting from p-tolylacetic acid and through an analogous series of intermediates. The latter were in general used without characterisation apart from threo-3-hydroxy-2-p-tolyl-4-penten-1-ol [NMR:2.3 (3H,s), 3.6 (1H,d), 4.6 (1H,q), 5.2 (2H,d), 5.7 (1H,m), 6.8 (2H,br s), 7.1 (4H,m)].

EXAMPLE 7

Using a similar procedure to that described in Example 2, but starting from 5(Z)-7-(2, 2-dimethyl-5-phenyl-1, 3-dioxan-trans-4-yl)heptenoic acid, there was obtained 7-(2, 2-dimethyl-5-phenyl-1,3-dioxan trans-4-yl)heptanoic acid as an oil, NMR: 1.0–1.6 (16H,m), 2.1–2.3 (2H,t), 2.7 (1H,m), 3.6–4.0 (3H,m), 7.2 (5H,m).

EXAMPLES 8–10

Using a similar procedure to that described in Example 4, the following compounds were obtained:

(Example 8): 7-(5'-phenyl-[cyclohexanespiro 2'1,3-dioxan]-trans-4'-yl)heptanoic acid, as an oil, NMR: 1.1–2.0 (20H,m), 2.3 (3H,m), 2.8 (1H,m), 3.8–4.2 (3H,m), 7.25 (5H,m); m/e (chemical ionisation): 280 [(HOCH$_2$)(Ph)C=CH.(CH$_2$)$_6$.CO$_2$H.NH$_4$ $^+$], 263 [(HOCH$_2$)(Ph)C=CH.(CH$_2$)$_6$.CO$_2$H$_2$ $^+$];

(Example 9): 7-([2,4-cis,4,5-trans)-2-methyl-5-phenyl-1,3-dioxan-4 yl)heptanoic acid, as an oil, NMR: 1.1–1.7 (13H,m), 2.3 (2H,t), 2.8 (1H,m), 3.6–4.2 (3H,m), 4.8 (1H,q), 7.2 (5H,m); m/e (chemical ionisation): 324 (M$^+$+NH$_4$), 307 (M$^+$+H); and (Example 10) : 7-([2,4-cis-4,5 trans)-2-methyl-5-o-tolyl-1,3 dioxan-4 yl]heptanoic acid, as an oil, NMR: 1.1–1.8 (13H,m), 2.2–2.4 (5H,m), 3.1 (1H,m), 3.6–4.1 (3H,m), 4.9 (1H,m), 7.1 (4H,m); m/e (chemical ionisation): 338 (M$^+$+NH$_4$), 321 (M$^+$+H).

Examples 8 and 9 were obtained starting from threo-8-hydroxy-9-hydroxymethyl-9-phenylnonanoic acid (Z) and cyclohexanone and acetaldehyde, respectively, omitting the lithium hydroxide hydrolysis step. Z was obtained as follows:

A mixture of 7-(2,2-dimethyl-5-phenyl-1,3-dioxan-trans-4-yl)heptanoic acid (105 mg.), tetrahydrofuran (5 ml.), water (5 ml.) and 2M hydrochloric acid (0.5 ml.) was left for 24 hours and then diluted with water (100 ml.). The aqueous mixture was extracted with ether. The extracts were dried (MgSO$_4$) and evaporated to give Z as an oil (92.5 mg); NMR : 1.1–1.8 (10H,m), 2.3 (2H,t), 2.8 (1H,m), 3.8–4.1 (3H,m), 4.7 (2H, br s), 7.2 (5H,s); m/e (chemical ionisation): 298 (M$^+$+NH$_4$), 281 (M$^+$+H), 280 (M$^+$+NH$_4$—H$_2$O).

Example 10 was obtained starting from methyl threo-8-hydroxy-9-hydroxymethyl-9-o-tolylnonanoate and acetaldehyde.

EXAMPLES 11–15

Using a similar procedure to that described in Example 3, the following compounds were obtained:

(Example 11): 5(Z)-7-([2,4-cis,4,5-trans]-2-t-butyl-5-o-tolyl-1,3 dioxan-4-yl)heptenoic acid, as a colourless oil; NMR: 1.0 (9H,s), 1.4–2.4 (11H,m), 3.0 (1H,m), 3.6–4.1 (3H,m), 4.3 (1H,s), 5.4 (2H,m), 7.1 (4H,m); m/e (chemical ionisation): 378 (M$^+$+NH$_4$), 361 (M$^+$+H);

(Example 12) : 7-([2,4-cis,4,5-trans]-2-n-propyl-5-o-tolyl-1,3-dioxan-4-yl)heptanoic acid, as a white solid, m.p. 67–68° C. (recrystallised from hexane); NMR: 1.0 (3H,t), 1.2–1.8 (14H,m), 2.2–2.4 (5H,m), 3.1 (1H,m), 3.6–4.2 (3H,m), 4.7 (1H,t), 7.1 (4H,m); m/e : 347 (M$^+$—H);

(Example 13) : 7-([2,4-cis-4,5-trans]-2-t-butyl 5-o-tolyl-1,3-dioxan-4 -yl)heptanoic acid, as a colourless oil which slowly solidified: NMR: 0.9 (9H,s), 1.1–1.8

(10H,m), 2.2–2.4 (5H,m), 3.0 (1H,m), 3.5–4.1 (3H,m), 4.2 (1H,s), 7.1 (4H,m): m/e : 361 (M+—H), 362 (M+), 363 (M+ +H);

(Example 14): 7-([2,4-cis-4,5-trans]-2-ethyl-5-o tolyl-1, 3-dioxan-4-yl)heptanoic acid, as a white solid, m.p 67°–69° C. (recrystallised twice from hexane); NMR: 1.0 (3H,t), 1.1–1.8 (12H,m), 2.2–2.4 (5H,m), 3.1 (1H,m), 3.6–4.1 (3H,m), 4.6 (1H,t), 7.1 (4H,m); and (Example 15): 5(Z)-7-([2,4-cis-4,5-trans]-2-isopropyl-5-o-tolyl-1,3-dioxan-4-yl)heptenoic acid, as a colourless oil; NMR: 1.0 (6H,d), 1.4–2.4 (12H,m), 3.1 (1H,m), 3.5–4.1 (3H,m), 4.35 (1H,d), 5.2–5.6 (2H,m), 7.1 (4H,m); m/e (chemical ionisation): 364 (M+ +NH4), 347 (M+ +H).

The starting materials were 5(Z)-7-(2,2-dimethyl-5-o-tolyl-1,3-dioxan-trans-4-yl)-heptenoic acid and 7-(2,2-dimethyl-5-o-tolyl-1,3-dioxan-trans-4-yl)heptanoic acid, respectively, and the appropriate aldehyde i.e. 2,2-dimethylpropionaldehyde, n-butyraldehyde, isobutyraldehyde or propionaldehyde.

EXAMPLE 16

A mixture of 7-([2,4-cis,4,5-trans]-2- isopropyl-5-o-tolyl-1,3-dioxan-4-yl)heptanoic acid (348 mg.), 4-N,N-dimethylaminopyridine (135 mg.), methanesulphonamide (105 mg.) and dichloromethane (20 ml.) was stirred and then treated with dicyclohexylcarbodiimide (227 mg.). After 3 days, oxalic acid was added until effervescence stopped. The mixture was concentrated in vacuo. The residue was triturated with ether. The mixture was separated by filtration and the filtrate washed with 0.4M hydrochloric acid, then with water, dried (MgSO4) and evaporated. The residue (353 mg.) was purified by column chromatography using ether as eluant to give N methanesulphonyl-7-([2,4-cis,4,5-trans]2-isopropyl- 5-o-tolyl-1,3-dioxan-4-yl)heptanamide, as a colourless oil; NMR: 0.9 (6H,d), 1.0–1.8 (11H,m), 2.1–2.3 (5H,m), 3.0 (1H,m), 3.2 (3H,s), 3.3–4.1 (3H,m), 4.3 (1H,d), 7.1 (4H,m), 8.2 (1H,m); m/e (chemical ionisation): 443 (M+ +NH4), 426 (M+ +H).

EXAMPLES 17–18

Using a similar procedure to that described in Example 16 the following sulphonamides were obtained:

(Example 17): N-ethanesulphonyl-7-([2,4-cis,4,5-trans]- 2 isopropyl 5-o-tolyl-1,3-dioxan 4-yl)heptanamide, as a colourless oil; NMR: 1.0 (6H,d), 1.1–2.4 (15H,m), 3.0–4.1 (6H,m), 4.4 (1H,d), 5.2–5.6 (2H,m), 7.1 (4H,m), 8.7 (1H,br s); m/e (chemical ionisation): 455 (M+ +NH4), 438 (M+ +H); and (Example 18): N-methanesulphonyl-5(Z)-7-([2,4-cis,4,5-trans]-2-isopropyl-5-o-tolyl-1,3-dioxan-4-yl)heptenamide, as a colourless oil; NMR: 1.0 (6H,d), 1.4–2.4 (12H,m), 3.0–4.2 (7H,m), 4.4 (1H,d), 5.2–5.6 (2H,m), 7.1 (4H,s), 8.6 (1H,br s); m/e (chemical ionisation): 441 (M+ +NH4), 424 (M+ +H).

EXAMPLES 19–22

Using an analogous procedure to that described in Example 1 but starting from the appropriate acetaldehyde derivative of formula II (n=1, Ra=Rb=methyl), the following compounds were obtained:

(Example 19) : 5(Z) 7-(2,2-dimethyl-5-o-chlorophenyl- 1,3-dioxan trans-4-yl)heptenoic acid, as a colourless oil; NMR: 1.45, 1.55 (6H,2s), 2.0–2.3 (8H,m), 3.4–3.6 (1H,m), 3.8–3.9 (2H,m), 4.0–4.2 (1H,m), 5.2–5.5 (2H,m), 7.1–7.5 (4H,m); m/e: 253 (M+ +H);

(Example 20): 5(Z)-7-(2,2-dimethyl-5-o-fluorophenyl-1,3- dioxan-trans-4-yl)heptenoic acid as a colourless oil; NMR: 1.2–2.5 (14H,m), 2.9–3.3 (1H.m), 3.6–4.3 (3H,m), 5.1–5.6 (2H,m), 6.8–7.5 (4H,m); m/e: 337 (M+ +H);

(Example 21): 5(Z)-7-(2,2-dimethyl-5-o-trifluoromethylphenyl-1,3-dioxan-trans-4-yl)heptenoic acid, as a colourless oil; NMR : 1.3–2.4 (14H,m), 3.0–3.5 (1H,m), 3.85 (2H,d), 3.95–4.3 (1H,m), 5.05–5.55 (2H,m), 6.9–7.9 (4H,m); m/e (chemical ionisation): 404 (M+ +NH4), 387 (M+ +H); and (Example 22): 5(Z)-7-([2,4-cis,4,5-trans]-2 trifluoromethyl-5-o-tolyl-1,3-dioxan-4-yl)heptenoic acid, as a colourless oil*; NMR: 1.3–1.8 (6H,m), 1.0–1.2 (2H,t), 2.3 (3H,s), 3.0–3.3 (1H,m), 3.5–4.2 (3H,m), 4.8–5.0 (1H,q), 5.2–5.4 (2H,m), 7.1 (4H,m); m/e (chemical ionisation): 390 (M+ +NH4), 373 (M+ +H).
[*Purified by conversion to its methyl ester by diazomethane treatment followed by column chromatography of the ester (eluant: 1:1 v/v dichloromethane/hexane) and hydrolysis with 2M sodium hydroxide followed by 2M hydrochloric acid].

The necessary acetaldehydes for Examples 19–21 were obtained using an analogous sequence of reactions to those described in the preparation of the acetaldehyde in Example 1, starting with the appropriate substituted phenylacetic acid. In general, the intermediates obtained were used without characterisation.

The necessary acetaldehyde derivative for Example 22 was obtained by oxidation [using the procedure described in part (e) of Example 1] of [2,4-cis,4,5-trans]-2-trifluoromethyl-5-o-tolyl-4-(2-hydroxyethyl)-1,3-dioxane. The latter compound was obtained by the following method:

A mixture of threo-3-hydroxy-2-o-tolyl-4-penten-1-ol (1.1 g.), p-toluenesulphonyl chloride (1.1g.) and triethylamine (0.75 ml.) in dichloromethane (25 ml.) was left for 18 hours and then added to water (100 ml.) The organic layer was separated, washed with water, dried (Na2SO4) and evaporated. The residue was purified by flash chromatography using dichloro methane as eluant to give threo-3-hydroxy-2-o-tolyl-4-penten-1-yl p-toluenesulphonate (W) as a white solid (1.8 g.), m.p. 62–63° C. (recrystallised from hexane).

Trifluoroacetaldehyde gas was passed into a solution of W (3.0 g.) in tetrahydrofuran (40 ml.) at −65° C. until 2 molecular equivalents (17.4 mM) had been absorbed. The mixture was allowed to attain ambient temperature and, after 1 hour at this temperature, potassium carbonate (2.4 g.) was added and the mixture was heated under reflux for 2 hours. The mixture was then added to ice-/water (100 ml.) and the whole extracted with ether (2×50 ml.). The combined extracts were washed with brine, dried (Na2SO4) and evaporated. The residue was purified by flash chromatography using 1:1 v/v dichloromethane/hexane as eluant to give 2-trifluoromethyl-5-o-tolyl-4-vinyl-1,3-dioxane (X) (670 mg.) as a mixture of isomers. X (570 mg.) was reacted with 9-BBN (4.5 ml. of 0.5M hexane solution), using the procedure described in part (d) of Example 1, to give [2,4-cis, 4,5-trans-]-2-trifluoromethyl-5-o-tolyl-4-(2-hydroxyethyl)-1,3-dioxane, as a colourless oil, NMR: 1.6–1.9 (3H,m), 2.3 (3H,s), 3.2 (1H,m), 3.7 (2H,t), 3.8–4.6 (3H,m), 5.0–5.3 (1H,q), 7.2 (4H,m).

EXAMPLE 23

A mixture of 7-(2,2-dimethyl-5-o-benzyloxyphenyl-1,3-dioxan-trans-4-yl)heptanoic acid (80 mg.) and 10% w/w palladium-on-charcoal (5 mg.) in ethanol (10 ml.) was stirred under hydrogen at atmospheric pressure. When no further hydrogen was absorbed, the catalyst was removed by filtration. The filtrate was evaporated and the residue was purified by flash chromatography to give 7-(2,2-dimethyl-5-o hydroxyphenyl-1,3-dioxan-trans-4- yl)heptanoic acid, as a colourless oil (40 mg.); NMR: 1.5–1.6 (6H,d), 1.1–1.7 (1OH,m), 2.3 (2H,t), 3.0 (1H,m), 3.3–4.0 (3H,m), 7.1 (4H,m); m/e : 336 (M+).

The starting material was obtained using the same general procedure as described in Example 4 but starting from o-benzyloxyphenylacetic acid.

EXAMPLES 24–27

Using a similar procedure to that described in Example 3, but starting from the appropriate 7-(2,2-dimethyl-5-substituted-phenyl-1,3-dioxan-trans-4-yl)-heptanoic or -5(Z)-heptenoic acid and isobutyraldehyde, there were obtained:

(Example 24): 7-([2,4 cis,4,5-trans]-2-isopropyl-5-o-hydroxyphenyl-1,3-dioxan-4-yl)heptanoic acid, as a colourless oil; NMR: 0.9–1.0 (6H,d), 1.1–1.5 (11H,m), 2.2–2.4 (2H,t), 3.3–3.6 (1H,m), 3.8–4.4 (3H,m), 4.35 (1H,d), 7.1 (4H,m); m/e (chemical ionisation): 368 (M+ +NH$_4$), 351 (M+ +H);

(Example 25): 5(Z)-7-([2,4-cis,4,5-trans]-2-isopropyl-5-o-fluorophenyl-1,3 dioxan-4-yl)heptenoic acid, as a pale yellow oil; NMR: 1.0 (6H,d), 1.4–2.4 (9H,m), 3.1–3.3 (1H,m), 4.4 (1H,d), 3.8 (1H,t), 3.85–4.0 (1H,m), 4.05 (1H,q), 5.25–5.6 (2H,m), 6.9–7.3 (4H,m); m/e : 350 (M+), 349 (M+—H), 307 (M+—C$_3$H$_7$);

(Example 26): 5(Z)-7-([2,4-cis,4,5-trans]-2-isopropyl-5-o-chlorophenyl-1,3-dioxan-4-yl)heptenoic acid, as a colourless oil; NMR: 0.95 (6H,d J=6Hz), 1.1–2.35 (9H,m), 3.1–3 5 (1H,m), 3.7 (1H,t J=10Hz), 3.8–4.2 (2H,m), 4.5 (1H,d J=5Hz), 5.2–5.6 (2H,m), 7.1–7.6 (4H,m); m/e: 367 (M+ +H), 277, 239, 138; and (Example 27): 5(Z)-7-([2,4-cis,4,5-trans]-2 -isopropyl-5-o-trifluoromethylphenyl-1,3-dioxan-4-yl)heptenoic acid, as a colourless oil; NMR: 0.8–1.2 (6H,d), 1.4–2.4 (9H,m), 3.0–4.2 (3H,m), 4.2–4.8 (2H,m), 5.2–5.5 (2H,m), 7.1–7.8 (4H,m); m/e : 357 (M+—C$_3$H$_7$), 273, 172.

EXAMPLE 28

7-(2,2-Dimethyl-5-phenyl-1,3-dioxan-trans-4-yl)heptanoic acid (0.50 g.) was reacted with an excess of an ethereal solution of diazomethane using a conventional procedure. Evaporation of the reaction mixture followed by flash chromatographic purification of the residue using chloromethane as eluant gave methyl 7-(2,2-dimethyl-5 phenyl-1,3-dioxan-trans-4-yl)heptanoate, as a colourless oil (0.40 g.); NMR: 1.0–1.5 (16H,m), 2.2–2.4 (2H,t), 2.6–3.0 (1H,m), 3.7 (3H,s), 3.8–4.2 (3H,m), 7.1–7.4 (5H,m); m/e : 319 (M+—CH$_3$), 245 (C$_{15}$H$_{21}$O$_2$+).

EXAMPLE 29

Using the same procedure as that described in Example 1, but starting from (+)-threo-3-hydroxy-2-o-tolyl-4-pentenoic acid (3.0 g.), there was obtained (+)-5(Z)-7-(2,2-dimethyl-5-o tolyl-1,3-dioxan trans-4-yl)heptenoic acid (0.4 g., 8.25% overall yield); optical rotations: $^{25}[\alpha]_{589}$+18.4°, $^{25}[\alpha]_{578}$+19.2°, $^{25}[\alpha]_{546}$+21.8°, $^{25}[\alpha]_{436}$+36.8° (c=1.34 in methanol).

The optically active starting material (from which the required acetaldehyde is obtained using steps (b)–(e) of Example 1) was obtained as follows:

A mixture of (+)-threo-3-hydroxy-2-o-tolyl-4-pentenoic acid ["A" in Example 4, recrystallised from toluene to give solid m.p. 121° C.] (20.0 g.), l-ephedrine (16.04 g.) and water (50 ml.) was warmed until a clear solution was formed. The solution was left at ambient temperature for 18 hours. The precipitate which formed was collected by filtration. The filtrate (Q) was retained. The solid was washed with a little water, and dried at 60° C. to give the l-ephedrine salt as a white crystalline solid (5.9 g.), m.p. 135–136° C. (after recrystallisation from ethyl acetate). This solid was partitioned between 2M hydrochloric acid and ether. The ether layer was separated and the aqueous layer extracted with ether. The combined extracts were washed successively with water and brine, dried (MgSO$_4$) and evaporated to give (—)-threo-3-hydroxy-2-o-tolyl-4-pentenoic acid as an oil which crystallised after some time to give solid (3.5 g.), m.p. 64.5–68° C.; optical rotations: $^{25}[\alpha]_{589}$—138.2°, $^{25}[\alpha]_{578}$—144.2°, $^{25}[\alpha]_{546}$—165.2° $^{25}[\alpha]_{436}$—294 6°, $^{25}[\alpha]_{365}$—497 7° (c=3.642, methanol).

The filtrate Q was diluted with water, acidified (2M hydrochloric acid) and extracted twice with ether. The extracts were washed with water, then brine, dried (MgSO$_4$) and evaporated. The white solid (13.4 g.) obtained was dissolved together with d-ephedrine (10.8 g.) in ethyl acetate (30 ml.). After 18 hours at ambient temperature a precipitate had formed and was collected by filtration to give the d-ephedrine salt as white crystals (9.4 g.), m.p.133.5°–136° C. (after recrystallisation from ethyl acetate). This salt was partitioned between 2M hydrochloric acid and ether as described for the l-ephedrine salt. In this way there was obtained (+)-threo-3-hydroxy-2-o-tolyl-4-pentenoic acid as an oil which slowly crystallised to give solid (4.4 g.), m.p. 65°–67° C.; optical rotations: $^{25}[\alpha]_{589}$ +135°, $^{25}[\alpha]_{578}$ +140.9°, $^{25}[\alpha]_{546}$ +161.5°, $^{25}[\alpha]_{436}$ +288.4°, $^{25}[\alpha]_{365}$ +487.7° (c=3.732, methanol).

EXAMPLE 30

An illustration of a pharmaceutical composition suitable for administration to man for therapeutic purposes is a capsule containing a compound of formula I (such as that described in Example 12) or a salt as appropriate (2–300 mg.) together with powdered lactose (596.5–298.5 mg.) and magnesium stearate (1.5 mg. ) i.e. 600 mg. of dry ingredients .

| Chemical Formulae |
|---|

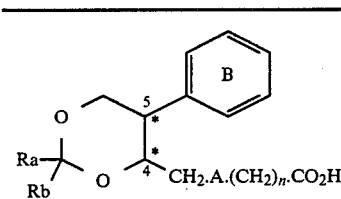

I

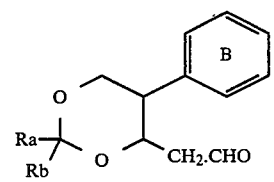

II

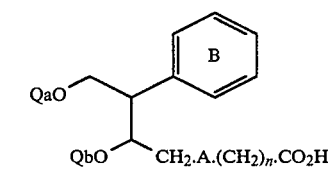

III

Chemical Formulae

IV

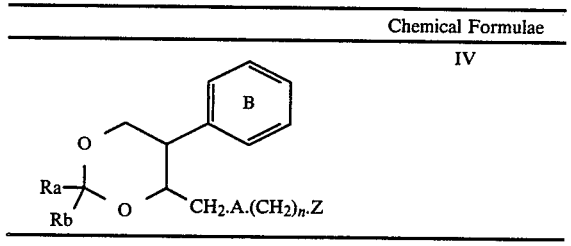

Reaction Scheme II -continued

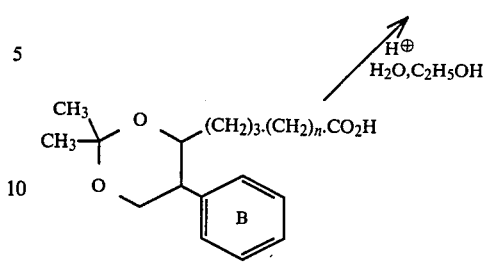

I (Ra = Rb = CH₃; A = CH₂CH₂)

Reaction Scheme I

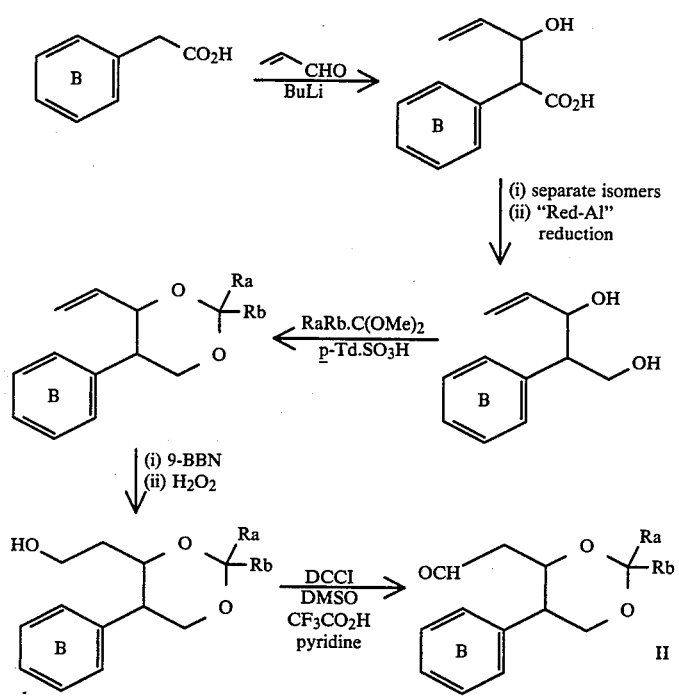

Reaction Scheme II

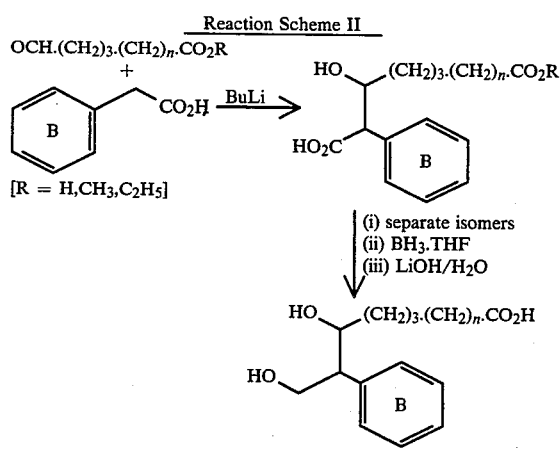

[R = H, CH₃, C₂H₅]

(i) separate isomers
(ii) BH₃.THF
(iii) LiOH/H₂O

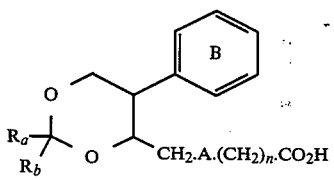

III (Qa = Qb = H; A = CH₂CH₂)

What is claimed is:

1. A (5-phenyl-1,3-dioxan-4-yl)alkenoic or alkanoic acid derivative of the formula I ![Formula I structure]

wherein: Ra is (1–6C)alkyl or halogeno(1–6C)alkyl; Rb is hydrogen, (1–6C)alkyl or halogeno(1–6C)alkyl; or Ra and Rb together form a polymethylene (2–4C)oxypolymethylene, mathyleneoxyethylene or ethyleneoxyethylene group; n is 2,3 or 4; A is vinylene or ethylene; benzene ring B optionally bears a 2-substituent selected from halogeno, methyl, hydroxy, trifluoromethyl and nitro, or bears a 4-methyl substituent; and the substituents at the 4 and 5 positions of the dioxane ring have trans-relative stereochemistry; or a pharmaceutically acceptable salt, (1–6C)alkyl ester or (1–6C)alkanesulphonamide of said compound of formula I.

2. A compound as claimed in claim 1 wherein Ra is methyl, ethyl, propyl, isopropyl, t-butyl, chloromethyl, 2-chloroethyl, trifluoromethyl or 2,2,2-trifluoroethyl, and Rb is hydrogen or one of the above values for Ra; or Ra and Rb together form trimethylene, tetramethylene, pentamethylene, trimethyleneoxy, methyleneoxyethylene or ethyleneoxyethylene; and benzene ring B optionally bears a 2-substituent selected from fluoro, chloro, bromo, methyl, hydroxy, trifluoromethyl and nitro, or bears a 4-methyl substituent.

3. A compound as claimed in claim 1 wherein n in 3 and A is ethylene or cis-vinylene.

4. A compound of the formula I

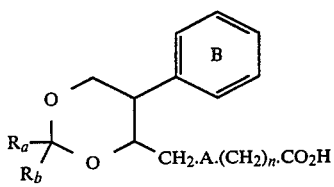

wherein: Ra is (1–4C)alkyl or trifluoromethyl; Rb is hydrogen; n is 3; A is ethylene or cis-vinylene; benzene ring B is selected from phenyl, o-tolyl and o-fluoro-, o-chloro-,o-hydroxy- and o-trifluoromethyl-phenyl; and the substituents at positions 4 and 5 of the dioxane ring have trans-relative stereochemistry; or a pharmaceutically acceptable salt, (1–6C)alkyl ester or (1–6C)alkanesulphonamide of said compound of formula I.

5. A compound selected from 7-([2,4-cis,4,5-trans]-2-isopropyl-5-o-tolyl-1,3-dioxan-4-yl)heptanoic acid, 7-([2,4-cis, 4,5-trans]-2-n-propyl-5-o-tolyl-1,3-dioxan-4-yl)heptanoic acid, 7-([2.4-cis-4,5-trans]-2-ethyl-5-o-tolyl-1,3-dioxan-4-yl)heptanoic acid, 5(Z)-7-([2,4-cis,4,5-trans]-2-trifluoromethyl- 5-o-tolyl-1,3-dioxan-4-yl)heptenoic acid, and the pharmaceutically acceptable salts, (1–6C) alkyl esters and (1–6C)alkanesulphonamides thereof 6. A salt as claimed in claim 1 which is selected from alkali metal, alkaline earth metal, aluminium and ammonium salts and from salts with organic amines and quaternary bases forming physiologically acceptable cations.

7. A (1–6C)alkyl ester as claimed in claim 1 which is selected from methyl, ethyl, propyl and butyl esters.

8. A (1–6C)alkanesulphonamide as claimed in claim 1 which is selected from methanesulphonamides and ethanesulphonamides.

9. A pharmaceutical composition useful for antagonising one or more of the actions of thromboxane A$_2$ in warm blooded animals requiring such treatment, said composition comprising a thromboxane A$_2$ antegonistically effective amount of a compound of the formula I or a pharmaceutically acceptable salt, (1–6C)alkyl ester or (1–6C) alkanesulphonamide thereof, as claimed in claim 1, together with a pharmaceutically acceptable carrier or diluent.

10. A method of antagonising one or more of the actions of thromboxane A$_2$ in a warm-blooded animal requiring such treatment which comprises administering to said animal a thromboxane A$_2$ antagonistically effective amount of a compound of the formula I, or a pharmaceutically acceptable salt, (1–6C)alkyl ester or (1–6C)alkanesulphonamide thereof, as claimed in claim 1.

* * * * *